United States Patent [19]

Umezawa et al.

[11] Patent Number: 4,699,879

[45] Date of Patent: Oct. 13, 1987

[54] PROCESS FOR MICROBIAL PRODUCTION OF AN OPTICALLY ACTIVE 3-(3,4-DIHYDROXYPHENYL)SERINE

[75] Inventors: Hamao Umezawa; Tomio Takeuchi, both of Tokyo; Toshiharu Nagatsu, Yokohama; Masa Hamada, Tokyo; Shuichi Iwadare, Tokyo; Ikuo Matsumoto, Tokyo; Hajime Morishima, Tokyo, all of Japan

[73] Assignees: Zaidan Hojin Biseibutsu Kagaku Kenkyu Kai; Banyu Pharmaceutical Co., both of Tokyo, Japan

[21] Appl. No.: 668,148

[22] Filed: Nov. 5, 1984

[30] Foreign Application Priority Data

Nov. 4, 1983 [JP] Japan .................................. 58-205859

[51] Int. Cl.$^4$ ......................... C12P 13/06; C07P 41/00
[52] U.S. Cl. .................................... 435/116; 435/280; 435/826; 435/886; 435/908
[58] Field of Search ............... 435/116, 280, 826, 886, 435/893, 908

[56] References Cited

U.S. PATENT DOCUMENTS

| | | | |
|---|---|---|---|
| 3,386,888 | 6/1968 | Chibata et al. ...................... | 435/280 |
| 3,546,070 | 12/1970 | Yoshinaga et al. ................. | 435/280 |
| 3,669,837 | 6/1972 | Parcell ................................ | 435/280 |
| 3,841,966 | 10/1974 | Soichiro Asai et al. ............ | 435/280 |

FOREIGN PATENT DOCUMENTS 1369462 10/1974 United Kingdom ................ 435/280

Primary Examiner—David M. Naff
Attorney, Agent, or Firm—Larson and Taylor

[57] ABSTRACT

N-acyl-DL-3-(3,4-dihydroxyphenyl)serine or a catecholic hydroxyl-protected derivative thereof is stereospecifically de-acylated by reaction with a microorganism of the genus Streptomyces or Streptoverticillium having an acylase or with an extract of said microorganism containing said acylase, to produce L-3-(3,4-dihydroxyphenyl)serine or the hydroxyl-protected derivative thereof, with the N-acyl-D-3-(3,4-dihydroxyphenyl)serine compound remaining unaltered. The L-3-(3,4-dihydroxyphenyl)serine compound so produced can be separated from the N-acyl-D-3-(3,4-dihydroxyphenyl)serine compound owing to the difference in the properties of them.

6 Claims, No Drawings

PROCESS FOR MICROBIAL PRODUCTION OF AN OPTICALLY ACTIVE 3-(3,4-DIHYDROXYPHENYL)SERINE

This invention relates to a process for the production of an optically active 3-(3,4-dihydroxyphenyl)serine which is known to be useful as a medicine, or an optically active 3-(3,4-dihydroxyphenyl)serine protected derivative in which the catecholic 3- and 4-hydroxyl groups on the phenyl ring have been protected and which is useful as an intermediate product for the production of an optically active 3-(3,4-dihydroxyphenyl)-N-methylserine.

It is known that L-threo-3-(3,4-dihydroxyphenyl) serine (sometime referred to as L-threo-DOPS) is useful as an anti-depressant agent or anti-hypertensive agent (see Japanese patent application unexamined first publication "Kokai" No. 49252/75; Japanese patent application unexamined first publication "Kokai" No. 20747/80; U.S. Pat. Nos. 3,920,728; 4,319,040) and also as an anti-parkinsonian agent (see Japanese patent application unexamined first publication "Kokai" No. 125630/77). It is known that L-erythro-3-(3,4-dihydroxyphenyl)serine is useful as an anti-hypertensive agent (see Japanese patent application unexamined first publication "Kokai" No. 49252/75). Further, such an L-threo-3-(3,4-dihydroxyphenyl)serine O-protected derivative in which the catecholic hydroxyl groups present at the metha- and para-positions of the phenyl ring each have been protected with a known hydroxyl-protective group is useful as a starting material for synthesis of L-threo-3-(3,4-dihydroxyphenyl)-N-methylserine which is interesting as psychotropic agent, especially anti-depressant agent and as anti-parkinsonian agent (see Japanese patent application No. 221797/82; U.S. patent application Ser. No. 523,957 and EPC patent application publication No. 0112606 A1). Such an L-erythro-3-(3,4-dihydroxyphenyl)serine O-protected derivative in which the catecholic 3- and 4-hydroxyl groups on the phenyl ring have been protected are useful also as a starting compound for synthesis of L-erythro-3-(3,4-dihydroxyphenyl)-N-methylserine which is interesting as anti-hypertensive agent (see Japanese patent application No. 72053/83).

For the production of an optically active, that is, L- or D-threo-3-(3,4-dihydroxyphenyl)serine, there are known several prior art methods which each comprise subjecting an optically inactive, that is, DL-threo-N-benzyloxycarbonyl-3-(3,4-dibenzyloxyphenyl)serine to optical resolution procedure using as the optically resolving agent an optically active ephedrine or an optically active threo-1-(p-nitrophenyl)-2-amino-1,3-propanediol (see Japanese patent application unexamined first publication "Kokai" No. 49252/75); quinine (see Japanese patent application unexamined first publication "Kokai" No. 65242/77); an optically active threo-1-(p-methylsulfonylphenyl)-2-amino-1,3-propanediol (see Japanese patent application unexamined first publication "Kokai" No. 36233/79) and optically active S-2-amino-1,1-diphenylpropanol, S-2-amino-3-methyl-1,1-diphenylbutanol or S-2-amino-4-methyl-1,1-diphenylpentanol (see Japanese patent application unexamined first publication "Kokai" No. 29551/81), respectively, and then removing the remaining N-protecting benzyloxycarbonyl group and catechol-protecting benzyl group from the optically active threo-N-benzyloxycarbonyl-3-(3,4-dibenzyloxyphenyl)serine so isolated. However, these prior art methods are commercially disadvantageous due to that the above-mentioned optically resolving agents are hardly available in commerce, that the L-3-(3,4-dihydroxyphenyl)serine of a high optical purity cannot be obtained without troublesome repetition of recrystallization and re-precipitation, and that an extra step of decomposing the resulting diastereomer salt as the intermediate product is needed.

In this situation, we, the present inventors, have examined whether or not DL-threo-3-(3,4-dihydroxyphenyl) serine can be optically resolved into the D-form and the L-form by an enzymatic method, and we have got an idea that a success may be attained if an N-acyl-DL-3-(3,4-dihydroxyphenyl)serine compound of the general formula

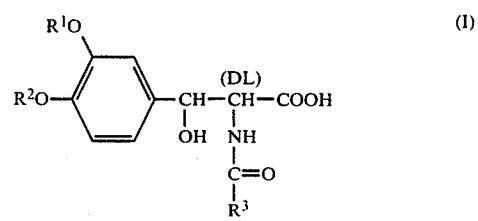

wherein $R^1$ and $R^2$ each denote a hydrogen atom or a hydroxyl-protecting group for the hydroxyl groups of catecholic nature present at the 3- and 4-positions of the phenyl ring and $R^3$ denotes an alkyl group or an aryl group which may optionally be substituted is prepared and is then reacted with such an acylase which is capable of removing hydrolytically the N-acyl group ($R^3CO-$) preferentially from the α-amino group of the L-isomer of said DL-compound of the formula (I) but is not capable of removing the N-acyl group from the α-amino group of the D-isomer of the DL-compound of the formula (I), so that there is produced an L-3-(3,4-dihydroxyphenyl)serine compound of the general formula

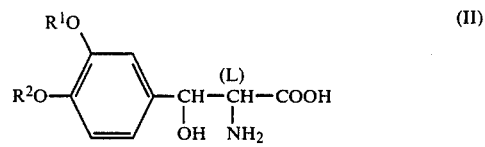

wherein $R^1$ and $R^2$ are as defined above, while the N-acyl-D-3-(3,4-dihydroxyphenyl)serine of the general formula (III)

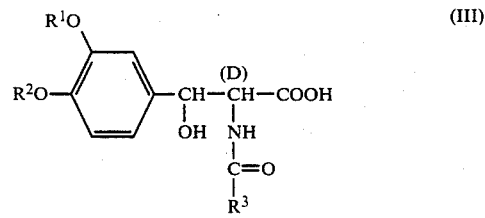

wherein $R^1$, $R^2$ and $R^3$ are as defined above remains unaltered. As a result of our experiments, we have found that all the known acylases which are presently available are not capable of removing the N-acyl group ($R^3CO-$) preferentially from the N-acyl-L-3-(3,4-dihydroxyphenyl) serine by asymmetrical hydrolysis. Accordingly, we have extensively studied about a variety of naturally occurring materials and substances and have now found that some microorganisms of the genus Streptomyces and some microorganisms of the genus Streptoverticillium are capable of removing hydrolytically the N-acyl group preferentially from the L-form of the N-acyl-3-(3,4-dihydroxyphenyl) serine which is present in the DL-compound of the general formula (I), and that these microorganisms of the genus Streptomyces and the genus Streptoverticillium have such acylase which is capable of hydrolysing preferetially the L-form of the threo- or erythro-N-acyl-3-(3,4-dihydroxyphenyl)serine to remove the N-acyl group therefrom.

Thus, we have found that the threo isomer or the erythro isomer of DL-3-(3,4-dihydroxyphenyl)serine as prepared by a known method, or such a DL-3-(3,4-dihydroxyphenyl)serine O-protected derivative having the catecholic 3- and 4-hydroxyl groups protected may be N-acylated with an alkanoyl group or an aroyl group in a known manner, and the N-acyl-DL-3-(3,4-dihydroxyphenyl)serine or the N-acyl-O-protected derivative thereof so produced may then be subjected to enzymatic reaction with a culture broth of a microorganism of the genus Streptomyces or the genus Streptoverticillium having the acylase, or with a material obtained from a treatment of said culture broth and containing the acylase, for example, the cells of the microorganism separated from said culture broth, and an enzyme material obtained from a treatment of said cells, or with the acylase itself produced by and extracted from said microorganism, so that the N-acylated serine product is stereoselectively hydrolysed to remove the N-acyl group therefrom, whereby the L-3-(3,4-dihydroxyphenyl)serine or its O-protected derivative having the catecholic 3- and 4-hydroxyl groups protected is produced, while the N-acyl-D-3-(3,4-dihydroxyphenyl)serine or its O-protected derivative having the 3- and 4-catecholic hydroxyl groups protected is remaining unaltered without receiving the enzymatic reaction; and also that the former, that is, the L-3-(3,4-dihydroxyphenyl)serine compound can be separated from the latter that is, the N-acyl-D-3-(3,4-dihydroxyphenyl)serine compound by utilizing different solubilities of them or any difference in other physico-chemical properties of them. On the basis of these findings, this invention has been accomplished.

According to an aspect of this invention, therefore, there is provided a process for producing an optically active L-3-(3,4-dihydroxyphenyl)serine compound of the formula (II)

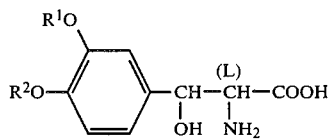

wherein $R^1$ and $R^2$ each are a hydrogen atom or a hydroxyl-protecting group for the catecholic 3- and 4-hydroxyl group on the phenyl ring, and an optically active D-3-(3,4-dihydroxyphenyl)serine compound of the formula (III)

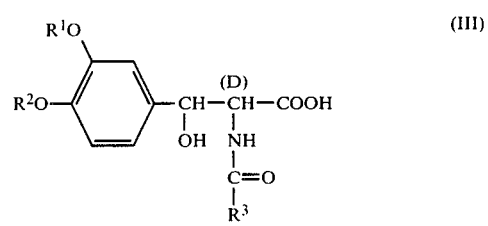

wherein $R^1$ and $R^2$ are as defined above and $R^3$ is unsubstituted or substituted alkyl group or an unsubstituted or substituted aryl group, which process comprises reacting an N-acyl-DL-3-(3,4-dihydroxyphenyl)serine compound of the general formula (I)

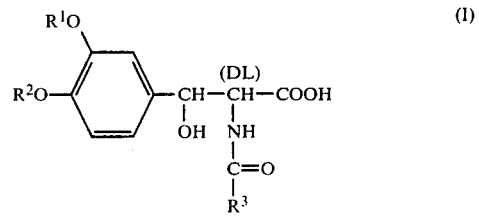

wherein $R^1$, $R^2$ and $R^3$ are as defined above, with a microorganism of the genus Streptomyces or the genus Streptoverticillium having an acylase capable of removing hydrolytically the N-acyl group ($-CO-R^3$) preferentially from the L-isomer of the DL-serine compound of the formula (I), or with an extract of said microorganism containing said acylase, to remove preferentially the N-acyl group ($-CO-R^3$) from the amino group of the L-isomer present in the DLserine compound of the formula (I) and thereby to produce the L-3-(3,4-dihydroxyphenyl)serine compound of the formula (II), and separating this L-serine compound (II) from the N-acyl-D-3-(3,4-dihydroxyphenyl)serine compound of the formula (III) which remains unaltered without being de-acylated.

If required, the process of this invention may further include a step of removing the residual hydroxyl-protecting groups $R^1$, $R^2$) from the resulting L-3-(3,4-dihydroxyphenyl)serine O-protected derivative of the formula (II) in a known manner to give L-3-(3,4-dihydroxyphenyl)serine, and/or a step of removing the N-acyl group ($-CO-R^3$) from the resulting N-acyl-D-3-(3,4-dihydroxyphenyl)serine compound of the formula (III), if necessary, followed by a further step of removing the residual hydroxyl-protecting groups ($R^1,R^2$) from the resultant D-3-(3,4-dihydroxyphenyl)serine O-protected derivative in a known manner to give D-3-(3,4-dihydroxyphenyl)serine. Thus, when the N-acyl-D-3-(3,4-dihydroxyphenyl)serine compound of the formula (III) as obtained in accordance with the process of this invention is hydrolyzed by a chemical agent in a known manner for removal of the N-acyl group therefrom, there is produced D-3-(3,4-dihydroxyphenyl)serine or its O-protected derivative having the catecholic 3- and 4-hydroxyl groups protected.

According to another aspect of this invention, there is provided a process for de-acylating stereo-selectively an N-acyl-L-3-(3,4-dihydroxyphenyl)serine compound of the formula (I')

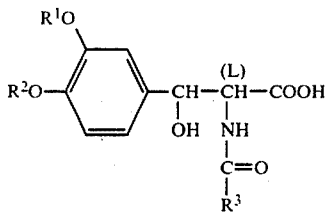

wherein $R^1$, $R^2$ and $R^3$ are as defined above, which process comprises reacting the N-acyl-L-3-(3,4-dihydroxyphenyl) serine compound (I') with a microorganism of the genus Streptomyces or the genus Streptoverticillium having an acylase capable of removing hydrolytically the N-acyl group ($-CO-R^3$) preferentially from the N-acyl-L-serine compound (I'), or with an extract of said microorganism containing said acylase, to remove said N-acyl group from the N-acyl-L-serine compound (I') and thereby to produce the L-3-(3,4-dihydroxyphenyl)serine compound of the formula (II)

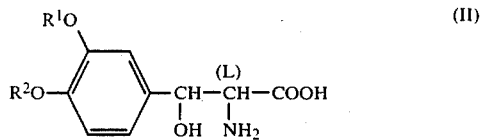

wherein $R^1$ and $R^2$ are as defined above.

In accordance with the process of this invention, any optically resolving chemical agent is not necessary, and besides, the step of decomposing the intermediate diastereomer salt as formed which was necessarily involved in the optical resolution procedure using an optically resolving chemical agent is not required owing to the use of the enzyme in the present process, so that an optically active 3-(3,4-dihydroxyphenyl)serine or its catecholic hydroxyl groups-protected derivative of high optical purity can readily be obtained by the process of this invention.

The process of this invention is now described in more detail. The microorganism which is used in accordance with this invention may be any strain belonging to the genus Streptomyes or the genus Streptoverticillium, as far as it is such microorganism which is capable of removing hydrolytically the N-acyl group ($R^3CO-$) selectively from the N-acyl-L-3-(3,4-dihydroxyphenyl)serine or a catecholic hydroxyl-protected derivative thereof which is present in the DL-serine compounds of the general formula (I) shown hereinbefore, or such microorganism which has or produces an acylase capable of removing hydrolytically said N-acyl group selectively from said N-acyl-L-3-(3,4-dihydroxyphenyl)serine or said catecholic hydroxyl-protected derivative thereof. Examples of such microorganism which may conveniently be used in the process of this invention include the following species: *Actinomyces aureoverticillatus* (IMC S-0234) (ISP 5080) (FERM P-7216) (ATCC 19726; CBS 465.68) (IFO 12742), *Actinomyces bicolor* (IMC S-0276) (ISP 5140) (ATCC 23614; CBS 469.68) (IFO 12746), *Streptomyces blastmyceticus* (IMC S-0189) (ISP 5029) (FERM P-7217) (ATCC 19731; CBS 470.68) (IFO 12747), *Streptomyces chartreusis* (IMC S-226) (ISP 5085) (ATCC 19738; CBS 476.68) (IFO 12753), *Streptomyces flavopersicus* (IMC S-0204) (ISP 5093) (ATCC 19756; CBS 494.68)(IFO 12769), *Actinomyces flavotricini* (IMC S-0219) (ISP 5152) (ATCC 23621; CBS 495.68) (IFO 12770), *Streptoverticillium griseocarneum* (IMC S-0237) (ISP 5004) (ATCC 19763; CBS 501.68) (IFO 12776), *Streptomyces hachijoensis* (IMC S-0244) (ISP 5114) (FERM P-7218) (ATCC 19769; CBS 507.68) (IFO 12782), *Streptomyces halstedii* (IMC S-0194) (ISP 5068) (ATCC 19770; CBS 508.68) (IFO 12783), *Streptoverticillium hiroshimense* (IMC S-0179) (ISP 5037) (FERM P-7252) (ATCC 19772CBS 510.68) (IFO 12785), *Streptomyces tendae* (IMC S-0168) (ISP 5101) (ATCC 19812; CBS 565.68) (IFO 12822), and *Streptomyces toyocaensis* (IMC S-0163) (ISP 5030) (FERM P-7253) (ATCC 19814; CBS 567.68) (IFO 12824) and others. All these microorganisms mentioned above are known stored type strain cultures of which microbiological properties are described in the "International Journal of Systematic Bacteriology" Volume 18, No. 2, pages 84–176 (April 1968). The disclosure of this book are incorporated herein by reference. All the above-mentioned microorganisms are publicly available from a Japanese depository "The Institute for Fermentation, Osaka (IFO) Organization" at 17-85 Juso-honmachi 2-chome, Yodogawa-ku, Osaka, 532, Japan, under IFO accession numbers which are mentioned in a catalogue "List of Cultures" 1984, 7th Edition, issued by the IFO, or from the "American Type Culture Collection", Washington D.C., U.S.A. The "IMC" numbers given to the above-mentioned microorganisms are the applicant's reference numerals of the cultures stored in the applicant's laboratory "Institute of Microbial Chemistry", Kami-Osaki, Meguro ku, Tokyo, Japan. The "ISP" numbers given to these microorganisms are the standard reference numerals alloted by "International Streptomyces Projects". Amongst the above-mentioned microorganisms, the strains having FERM P-7216, FERM P-7217 and FERM P-7218 as the F.R.I. deposit numbers were deposited on 5th Sept. 1983 in the Japanese depository "Fermentation Research Institute", Agency of Industrial Science and Technology, Japan and now deposited there under the accession numbers "FERM BP-640", "FERM BP-641" and "FERM BP-642", respectively, since 18th Oct. 1984 under the Budapest Treaty. The strains having FERM P-7252 and FERM P-7253 were deposited on 20th Sept. 1983 in the "Fermentation Research Institute" and now deposited there under "FERM BP-643' and 'FERM BP-644", respectively, since 18th Oct. 1984 under the Budapest Treaty.

In the process of this invention, the starting substrate compound of the formula (I) may be reacted with the microorganism as used in accordance with this invention, by being contacted with said microorganism which is present in the culture broth of said microorganism. To prepare the culture broth of the microorganism, the microorganism is cultivated in a known manner using conventional culture media. The carbon sources present in the culture medium used may be usual ones e.g. glucose, saccharose, fructose, mannose, starch, molasses and the like, and the nitrogen sources may be usual ones e.g. organic ones such as peptone, meat extract, yeast extract, corn steep liquor, urea and the like, and/or inorganic nitrogen compounds such as aqueous ammonia, ammonium sulfate, sodium nitrate and the like. Such culture media further containing appropriate quantities of inorganic salts such as magnesium sulfate, sodium chloride, mono-potassium phosphate, di-potassium phosphate and the like certain compounds required for good growth of the microorganism, and/or additive substances for derivation of the enzyme are preferred. The cultivation of the microorganism may preferably be carried out under aerobic conditions, e.g. by incubation under aeration and stirring. Preferred cultivation temperatures may be in a range of 20° to 40° C. The cultivation duration may normally be in a range of 1 day to 10 days in many instances. In the process of this invention, the microorganism used and the culture broth of the microorganism serve as the source for the acylase which participates in the enzymatic de-acylation reaction involved in the present process. In place of using the microorganism or the culture broth containing the microorganism, it is also feasible to use the cells which have been separated from the culture broth in the intact state, which may be live or dead or which may also have been immobilised in a manner known for the techniques for immobilisation of microbial cells. The process of this invention may also be performed using an extract of said microorganism containing said acylase. This acylase-containing extract of the microorganism may be in the form of such filtrate of the culture broth of the microorganism, such material obtained from treatment of the cells, particularly a cell homogenate wherein the acylase is existing, or a solution of the acylase which has been isolated in crude or pure form. This solution of the acylase may be a solution of a crude enzyme (the acylase) which has been recovered from the culture broth or the cells of the microorganism by fractional precipitation method with ammonium sulfate, or a solution of a purified enzyme (the acylase) which has been purified by a gel-filtration method or other known purification method for enzymes. The recovery and purification of the enzyme may be achieved according to any known method for preparing acylases.

The N-acyl-DL-3-(3,4-dihydroxyphenyl)serine or a catecholic hydroxyl-protected derivative thereof according to the general formula (I) employed as the starting compound in the process of this invention may be prepared by reacting a carboxylic acid of the general formula (IV)

$$R^3COOH \quad (IV)$$

wherein $R^3$ is as defined above, or a reactive derivative (a functional equivalent) thereof, such as the acid chloride and acid anhydride, in the presence or absence of a condensation agent or catalyst, with DL-3-(3,4-dihydroxyphenyl)serine which may be produced by previously known methods (see "J. Chem. Soc." pp. 658–662 (1947); "J. Am. Chem. Soc." 76, pp. 1322–1326 (1954); "Chem. Ber." 87, pp. 892–901 (1954)), or with a catecholic hydroxyl-protected derivative of DL-3-(3,4-dihydroxyphenyl)serine. The N-acyl group ($R^3CO-$) as used may preferably be acetyl group, chloroacetyl group, glycolyl group, benzoyl group and the like, though any acyl group may be used in accordance with this invention as long as it is cleavable preferentially by the enzymatic reaction of the present process.

The starting N-acyl-DL-3-(3,4-dihydroxyphenyl) serine or a catecholic hydroxyl-protected derivative thereof according to the general formula (I) used as the starting compound contains two asymmetrical carbon atoms in the molecule thereof, so that there exist two isomers of the threo form and the erythro form. The threo-isomer or the erythro-isomer or even a mixture of them may be employed as the starting substrate in the process of this invention.

The starting DL-serine compound of the general formula (I) which serves as the substrate in the enzymatic de-acylation reaction of the present process may either be protected or unprotected at its catecholic 3- and 4-hydroxyl groups on the phenyl ring, depending on the purposes for which the de-acylated product of the present process is utilized. Thus, for example, when an optically active 3-(3,4-dihydroxyphenyl)serine is to be obtained, the catecholic hydroxyl groups of the substrate serine compound (I) may be unprotected. On the other hand, when it is ultimately desired to obtain an optically active 3-(3,4-dihydroxyphenyl)-N-methylserine by a subsequent N-methylation process, the enzymatic reaction in the process of this invention may preferably be conducted using the starting DL-serine compound of the general formula (I) in the form of the hydroxyl-protected derivative thereof, because the catecholic hydroxyl groups of the serine compound must have been protected for the subsequent N-methylation process. When the process of this invention is carried out using a catecholic hydroxyl-protected derivative of the N-acyl-DL-3-(3,4-dihydroxylphenyl)serine, an optically active 3-(3,4-dihydroxyphenyl) serine can, of course, be obtained readily by removing the hydroxyl-protecting groups from the de-acylated product by a conventional deprotection technique after the enzymatic reaction of the present process was achieved. The hydroxyl-protecting groups ($R_1$, $R_2$) available for protection of the catecholic 3- and 4-hydroxyl groups of the starting N-acyl-DL-serine compound (I) may be any of the hydroxyl-protecting groups which are conventionally employed for blocking the catecholic hydroxyl groups, for example, an aralkyl group such as benzyl, an alkoxycarbonyl group such as ethoxycarbonyl, an alkylidene group such as methylene and isopropylidene, or a cycloalkylidene group such as cyclohexylidene. A most preferred one is benzyl group. When an alhylidene group or a cycloalkylidene group is employed for the protection of the catecholic hydroxyl groups, the groups $R^1$ and $R^2$ taken together form a single alkylidene or cycloalkylidene group.

In the process of this invention, the enzymatic reaction of reacting the starting N-acyl-DL-serine compound of the formula (I) with the microorqanism or the acylase of said microorganism may preferably be carried out at a pH of 5 to 9, desirably at a pH of 6 to 5 and at a temperature of 20° to 80° C., desirably 35° to 60° C. The reaction medium may be water not containing or containing, if necessary, a proportion of an organic solvent which does not inactivate the enzyme, such as a lower alkanol, e.g. ethanol. If required or if preferred, the enzymatic reaction may be conducted in the presence of cation of a metal such as cobalt as the catalyst added. The required reaction time may vary depending on the quantity and the activity of the enzyme used, the reaction temperature and other various factors, but normally the reaction may be conducted for a time of 30 minutes to 20 hours. A reaction time of 2 hours to 18 hours will suffice in many cases.

The step of the enzymatic reaction may be followed by the step of separating the resultant L-3-(3,4-dihydroxyphenyl)serine or the catecholic hydroxyl-protected derivative thereof according to the general formula (II) from the N-acyl-D-3-(3,4-dihydroxyphenyl)serine or the catecholic hydroxyl-protected derivative thereof according to the general formula (III) which remains without receiving the enzymatic de-acylation. This separation may be performed by a precipitation method utilizing the fact that generally, the N-acyl-D-3-(3,4-dihydroxyphenyl)serine compounds are less soluble than the L-3-(3,4-dihydroxyphenyl)serine compounds in an aqueous medium at acidic pH range. Alternatively, the separation of the L-serine compound (II) from the N-acyl-D-serine compound (III) may be achieved by a transfer-dissolution method, as illustrated by Example 2 given later, in such a manner that the enzymatic reaction solution is extracted with n-butanol to afford a solution of both the L-compounds of the formula (II) and the D-compound of the formula (III) in n-butanol, the n-butanol is evaporated off from said solution, the resultant residue is taken up into 0.05M phosphate buffered solution (pH 7.0), the resulting solution containing the compounds (II) and (III) is adjusted to acidic pH with hydrochloric acid and then extracted with ethyl acetate to transfer mainly the compound (III) into ethyl acetate, the ethyl acetate extract is in turn, extracted with alkaline water (pH 9) to transfer the compound (III) into the aqueous phase which is then again extracted with ethyl acetate under the acidic condition (pH 1), and so on.

The final products (II) and (III) as obtained by the process of this invention each may further be isolated and purified by an ordinary chromatographic method such as silica gel column chromatography and ion-exchange resin chromatography. It is also possible to make isolation and purification of the final products in a very easy way e.g. by precipitation method or crystallization method with utilizing the difference in the solubilities of these products (II), (III).

This invention is now illustrated with reference to the following Examples to which this invention is not limited in any way.

EXAMPLE 1

(a) A culture medium comprising 1% potato starch, 1% glucose, 0.75% meat extract, 0.75% polypeptone, 0.3% sodium chloride, 0.1% magnesium sulfate hepta-hydrate, 0.0007% copper sulfate penta-hydrate, 0.0001% ferrous sulfate hepta-hydrate, 0.0008% manganese chloride tetrahydrate and 0.0002% zinc sulfate hepta-hydrate was placed in 100 ml-portions into 500 ml-conical flasks, and the culture medium was then inoculated with a loopful quantity of a slant culture of *Streptomyces hachijoensis* (IMC S-0244) (ISP 5114) (FERM P-7218) (FERM BP-642). The shaken incubation was made at 27° C. for 3 days to prepare a seed culture broth. This seed culture (10 ml) was inoculated into the culture medium of the same composition as described above which was charged in 1 l-portions into 5 l-conical flasks, and shaken incubation was made at 27° C. for 4 days. The culture broth obtained was filtered to remove the microbial cells, and to the resulting broth filtrate (3 l) was added ammonium sulfate in small portions to 80% saturation under stirring. The mixture was allowed to stand in a cold chamber at 5° C. overnight, and then centrifuged at 9,000 r.p.m. under cooling to 5° C. The deposited precipitate comprising the enzyme was collected and dissolved in 150 ml of 0.05M phosphate buffered solution to afford a solution of a crude enzyme (the acylase).

(b) Water (60 ml) was added to 1 g of DL-threo-N-acetyl-3-(3,4-dibenzyloxyphenyl)serine, and to the resulting aqueous suspension was added 30% aqueous sodium hydroxide dropwise until the DL-serine compound dissolved in water to give a clear solution. To this solution were added 20 ml of 0.5M phosphate buffered solution (pH 7.0) and a volume of water to a total volume of 90 ml to prepare a solution of the substrate serine compound. This solution of the substrate was admixed with 10 ml of the enzyme solution prepared as above and then was incubated at 37° C. for 18 hours for the enzymatic reaction. After the reaction, the reaction solution was filtered to remove the precipitate as formed. The filtrate obtained was adjusted to pH 1 by addition of hydrochloric acid and the precipitate so deposited was recovered by filtration to afford 150 mg of D-threo-N-acetyl-3-(3,4-dibenzyloxyphenyl)serine as a first crop. The first precipitate which was obtained by filtration of said reaction solution was taken up into 0.1N hydrochloric acid under heating. The resultant solution was allowed to stand at ambient temperature, thereby depositing a precipitate. This precipitate was separated from the liquid phase by filtration to give 240 mg of D-threo-N-acetyl-3-(3,4dibenzyloxyphenyl)serine as a second crop. These crop products showed $[\alpha]_D^{20}$ −20.9° (c 1, ethanol). The filtrate which remained after the separation of the D-isomer second crop (240 mg) by filtration was extracted with n-butanol, the extract in n-butanol was distilled under reduced pressure to remove the n-butanol, and the residue was crystallized out of isopropanol to afford 360 mg of L-threo-3-(3,4-dibenzyloxyphenyl)serine hydrochloride which showed $[\alpha]_D^{20}$ −5.99° (c 1, ethanol).

(c) The D-threo-N-acetyl-3-(3,4-dibenzyloxyphenyl) serine obtained as above was dissolved in a liquid mixture of 1N hydrochloric acid-methanol (1:1 by volume) and the resulting solution was heated for 5 hours under refluxing to effect the removal of the N-acetyl group, affording D-threo-3-(3,4-dibenzyloxyphenyl)serine. While, the L-threo-3-(3,4-dibenzyloxyphenyl)serine hydrochloride obtained as above was dissolved in ethanol and then catalytically reduced (hydrogenolysis) under hydrogen gas at 1 atm. at ambient temperature in the presence of 10% palladium-on-carbon to effect the removal of the hydroxyl-protecting benzyl groups, thereby affording L-threo-3-(3,4-dihydroxyphenyl)serine. Yield 100%.

EXAMPLE 2

(a) The culture medium of the same composition as used in Example 1 was inoculated with a loopful amount of a slant culture of *Actinomyces aureoverticillatus* (IMC S-0243) (ISP 5080) (FERM P-7216) (FERM BP-640) and the incubation was made at 27° C. for 5 days. The culture broth obtained was filtered to remove the microbial cells, and the resulting broth filtrate (100 ml) containing the acylase was mixed with 108 mg of DL-erythro-N-acetyl-3-(3,4dibenzyloxyphenyl)serine. The mixture was incubated at 37° C. for 18 hours to effect the enzymatic reaction.

(b) After the completed reaction, the reaction solution was adjusted to pH 2 by addition of hydrochloric acid and then extracted with n-butanol. The extract in n-butanol was distilled under reduced pressure to remove the n-butanol, and the residue was taken up into 0.05M phosphate buffered solution (pH 7.0). The solution so obtained was again adjusted to pH 2 with aqueous HCl and then extracted with ethyl acetate. The resulting organic extract containing D-erythro-N-acetyl-3-(3,4-dibenzyloxyphenyl)serine as transferred into ethyl acetate was mixed with a volume of water, and the mixture was adjusted to pH 9 by addition of aqueous sodium hydroxide, so that the D-erythro-N-acetyl-3-(3,4-dibenzyloxyphenyl)serine was transferred into the aqueous phase. The aqueous phase was subsequently adjusted to pH 1 with hydrochloric acid and again extracted with ethyl acetate. This extract in ethyl acetate was distilled under reduced pressure to remove the ethyl acetate, giving 34 mg of D-erythro-N-acetyl-3-(3,4-dibenzyloxyphenyl)serine. $[\alpha]_D^{20}$ −14.6° (c 1, ethanol).

(c) The aqueous phase which remained after the ethyl acetate extraction of the HCl-acidfied solution at pH 2 of the aforesaid residue as obtained in the above procedure (b) was extracted with n-butanol. The resultant extract in n-butanol was distilled under reduced pressure to remove the n-butanol, and the residue was mixed with methanol. The mixture was filtered to remove the insoluble matters therefrom, and the filtrate was distilled under reduced pressure to remove the methanol. Crystallization of the so obtained residue from isopropanol gave 26 mg of L-erythro-3-(3,4-dibenzyloxyphenyl)serine hydrochloride. $[\alpha]_D^{20}$ +19.5° (c 1, ethanol).

When this L-erythro-3-(3,4-dibenzyloxyphenyl)serine hydrochloride was subjected to catalytic hydrogenolysis in the same manner as in Example 1(c) to effect the removal of the hydroxyl-protecting benzyl groups, L-erythro-3-(3,4-dihydroxyphenyl)serine was obtained in a yield of 100%.

EXAMPLE 3

DL-Threo-N-acetyl-3-(3,4-dibenzyloxyphenyl)serine, DL-threo-N-chloroacetyl-3-(3,4-dibenzyloxyphenyl)serine, DL-threo-N-glycolyl-3-(3,4-dibenzyloxyphenyl)serine, DL-threo-N-benzoyl-3-(3,4-dibenzyloxyphenyl)serine, DL-threo-N-acetyl-3-(3,4-methylenedioxyphenyl)serine, DL-threo-N-acetyl-3-(3,4-dihydroxyphenyl)serine or DL-erythro-N-acetyl-3-(3,4-dibenzyloxyphenyl)serine was dissolved or suspended at the concentration of 2 mg/ml in 0.1M phosphate buffered solution (pH 7.0) to prepare different solutions of the substrates (the starting DL-serine compounds). The solution of the substrate (0.5 ml) was mixed with 0.5 ml of the enzyme solution which was prepared according to the procedure of Example 1(a) and which was containing the acylase of the microorganism, Streptomyces hachijoensis. The mixture so obtained was incubated at 37° C. for 17 hours for the enzymatic reaction to effect the removal of the N-acyl group (the de-acylation) from the substrate compound.

After the reaction, the reaction solution was analysed by high performance liquid chromatography with a column of "Nucleosil" 5 C$_{18}$ (4.6 mm×125 mm) to determine the yield of the de-acylation product which was produced by the removal of the N-acyl group from the substrate compound through the stereoselective enzymatic reaction involved. The results obtained are summarized in Table 1 below.

TABLE 1

| Substrate | Yield (%) of De-acylation product |
| --- | --- |
| DL-threo-N—acetyl-3-(3,4-dibenzyloxyphenyl)serine | 100 |
| DL-threo-N—chloroacetyl-3-(3,4-dibenzyloxyphenyl)serine | 100 |
| DL-threo-N—glycolyl-3-(3,4-dibenzyloxyphenyl)serine | 31 |
| DL-threo-N—benzoyl-3-(3,4-dibenzyloxyphenyl)serine | 10 |
| DL-threo-N—acetyl-3-(3,4-methylenedioxyphenyl)serine | 68 |
| DL-threo-N—acetyl-3-(3,4-dihydroxyphenyl)serine | 20 |
| DL-erythro-N—acetyl-3-(3,4-dibenzyloxyphenyl)serine | 81 |

In the above table, the "Yield (%) of De-acylation product" was calculated according to the following equation:

Yield (%) of De-acylation product =
$$\frac{\text{Molar numbers of the de-acylation product as formed}}{\text{Molar number of the substrate compound}} \times 2 \times 100$$

EXAMPLE 4

The culture medium of the same composition as used in Example 1 was inoculated with a loopful quantity of a slant culture of Actinomyces aureoverticillatus (IMC S-0234) (ISP 5080) (FERM P-7216) (FERM BP-640); Streptomyces blastmyceticus (IMC S-0189) (ISP 5029) (FERM P-7217) (FERM BP-641); or Streptomyces hachijoensis (IMC S 0244) (ISP 5114) (FERM P-7218) (FERM BP-642), and the shaken incubation was made at 27° C. for 4 days. The culture broth obtained was filtered to remove the microbial cells, and the resultant broth filtrate (0.5 ml) containing the acylase was mixed with 0.5 ml of the substrate solution comprising a solution containing DL-threo-N-acetyl-3(3,4-dibenzyloxyphenyl)serine at a concentration of 2 mg/ml in 0.1 M phosphate buffered solution (pH 7.0). The mixture was incubated at 37° C. for 17 hours to effect the enzymatic reaction.

After the completed reaction, the reaction mixture was made acidic by addition of 0.1 ml of 1N hydrochloric acid and then extracted with two 1 ml-portions of n-butanol. The combined extracts in n-butanol were distilled under reduced pressure to remove the n-butanol. The residue was dissolved in 1 ml of a mixture of 0.1M phosphoric acid and methanol (40:60 by volume), and the resultant solution was analysed by a high performance liquid chromatography with the same "Nucleosil 5 C$_{18}$" column as used in Example 3, to determine the yield of the de-acylation product as formed, namely the L-threo-3-(3,4-dibenzyloxyphenyl)serine.

The results obtained are tabulated in Table 2 below.

TABLE 2

| Strain | Yield (%) of De-acylation product |
| --- | --- |
| Actinomyces aureoverticillatus (ISP 5080) (FERM BP-640) | 75 |
| Streptomyces blastmyceticus (ISP 5029) (FERM BP-641) | 54 |
| Streptomyces hachijoensis (ISP 5114) (FERM BP-642) | 92 |

In the above table, the "Yield (%) of De-acylation product" was calculated according to the following equation:

Yield (%) of De-acylation product =
$$\frac{\text{Molar numbers of the de-acylation product as formed}}{\text{Molar numbers of the substrate compound}} \times 2 \times 100$$

EXAMPLE 5

The procedures of Example 4 were repeated but using the other strains. The results obtained are summarized in Table 3 below.

TABLE 3

| Strain | Yield (%) of De-acylation product |
|---|---|
| Streptoverticillium hiroshimense (ISP 5037) (FERM BP-643) | >30 |
| Streptomyces toyocaensis (ISP 5030) (FERM BP-644) | >30 |
| Actinomyces bicolor (ISP 5140) | >30 |
| Streptomyces chartreusis (ISP 5085) | >30 |
| Streptomyces flavopersicus (ISP 5093) | >30 |
| Actinomyces flavotrichini (ISP 5152) | >30 |
| Streptoverticillium griseocarneum (ISP 5004) | >30 |
| Streptomyces halstedii (ISP 5068) | >30 |
| Streptomyces tendae (ISP 5101) | >30 |

What we claim is:

1. A process for producing an optically active L-3-(3,4-dihydroxyphenyl)serine compound of the formula (II)

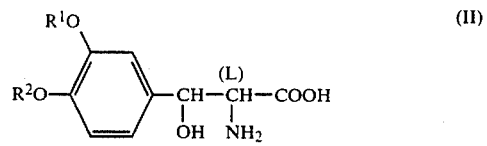

wherein $R^1$ and $R^2$ each are a hydrogen atom such that $-OR^1$ and $-OR^2$ are catecholic 3- and 4-hydroxyl groups, or $R^1$ and $R^2$ each are a hydroxyl-protecting group for the catecholic 3- and 4-hydroxyl groups, and an optically active N-acyl-D-3-(3,4-dihydroxyphenyl)serine compound of the formula (III)

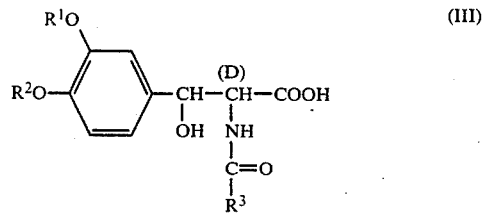

wherein $R^1$ and $R^2$ are as defined above and $R^3$ is an unsubstituted or substituted alkyl group or an unsubstituted or substituted aryl group, which process comprises reacting an N-acyl-DL-3-(3,4-dihydroxyphenyl)serine compound of the general formula (I)

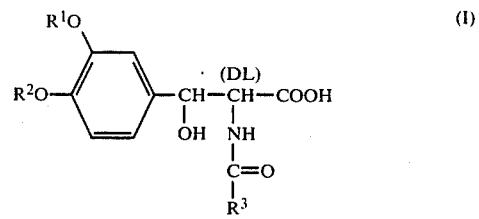

wherein $R^1$, $R^2$ and $R^3$ are as defined above, with a microorganism having an acylase or with an extract of said microorganism containing said acylase capable of removing hydrolytically the N-acyl group ($-CO-R^3$) from the L-isomer of the DL-serine compound of the formula (I), and thereby to produce the L-3-(3,4-dihydroxyphenyl)serine compound of the formula (II), and separating this L-serine compound (II) from the N-acyl-D-3-(3,4-dihydroxyphenyl)serine compound of the formula (III) which remains unaltered without being de-acylated, said microorganism being selected from the group consisting of Actinomyces aureoverticillatus ATCC 19726; Actinomyces bicolor ATCC 23614; Streptomyces blastmyceticus ATCC 19731; Streptomyces chartreusis ATCC 19738; Streptomyces flavopersicus ATCC 19756; Actinomyces flavotricini ATCC 23621; Streptoverticillium griseocarneum ATCC 19763; Streptomyces hachijoensis ATCC 19769; Streptomyces halstedii ATCC 19770; Streptoverticillium hiroshimense ATCC 19772, Streptomyces tendae ATCC 19812; and Streptomyces toyocaensis ATCC 19814.

2. A process as claimed in claim 1, wherein the hydroxyl-protecting groups $R^1$ and $R^2$ of formula (I) are each a benzyl group and $R^3$ is a methyl group, a chloromethyl group, a hydroxymethyl group or a phenyl group.

3. A process as claimed in claim 1, wherein the hydroxyl-protecting groups $R^1$ and $R^2$ of formula (I) taken together form a single alkylidene or cycloalylidene group.

4. A process as claimed in claim 1, wherein $R^1$ and $R^2$ of formula (I) are each a hydrogen atom and $R^3$ is a methyl group, a chloromethyl group, a hydroxymethyl group or a phenyl group.

5. A process as claimed in claim 1, in which the microorganism is Actinomyces aureoverticillatus ATCC 19726, Streptomyces blastmyceticus ATCC 19731 Streptomyces hachijoensis ATCC 19772, Streptomyces hiroshimense ATCC 19772 or Streptomyces toyocaensis ATCC 19814.

6. A process as claimed in claim 1, in which the reaction of an N-acyl-DL-3-(3,4-dihydroxyphenyl)serine compound of the formula (I) with the microorganism or with the extract of the microorganism containing the acylase is carried out at a temperature of 20° to 80° C., at a pH of 5 to 9 and for a time of 30 minutes to 18 hours.

* * * * *